(12) United States Patent
Raab et al.

(10) Patent No.: US 9,254,364 B2
(45) Date of Patent: Feb. 9, 2016

(54) ASSEMBLY FOR A DRUG DELIVERY DEVICE

(75) Inventors: Steffen Raab, Frankfurt am Main (DE); Sandra Arnhold, Büttelborn (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 962 days.

(21) Appl. No.: 13/498,226

(22) PCT Filed: Sep. 28, 2010

(86) PCT No.: PCT/EP2010/064330
§ 371 (c)(1),
(2), (4) Date: Aug. 3, 2012

(87) PCT Pub. No.: WO2011/039163
PCT Pub. Date: Apr. 7, 2011

(65) Prior Publication Data
US 2012/0289909 A1 Nov. 15, 2012

(30) Foreign Application Priority Data
Sep. 29, 2009 (EP) ..................................... 09171596

(51) Int. Cl.
*A61M 5/00* (2006.01)
*A61M 5/315* (2006.01)

(52) U.S. Cl.
CPC ....... *A61M 5/31535* (2013.01); *A61M 5/31553* (2013.01); *A61M 5/31556* (2013.01); *A61M 5/31585* (2013.01)

(58) Field of Classification Search
CPC .............. A61M 5/24; A61M 5/31551; A61M 5/31541; A61M 5/31585; A61M 5/3155; A61M 5/31583
USPC ........................... 604/211, 207, 208, 218, 232
See application file for complete search history.

(56) References Cited

U.S. PATENT DOCUMENTS 6,004,297 A * 12/1999 Steenfeldt-Jensen  A61M 5/31551
604/207
7,918,832 B2 * 4/2011 Veasey ............... A61M 5/31585
604/207

FOREIGN PATENT DOCUMENTS

WO 9938554 A1 8/1999
WO 2009080775 A1 7/2009

OTHER PUBLICATIONS

International Preliminary Report on Patentability for Int. App. No. PCT/EP2010/064330, mailed Apr. 12, 2012.

*Primary Examiner* — Phillip Gray
(74) *Attorney, Agent, or Firm* — Fish & Richardson P.C.

(57) ABSTRACT

An assembly for a drug delivery device (1), comprises a housing (2), a dose member (22), a guide track (42) and a spring member (26). The dose member (22) is adapted to be rotated in a dose setting direction with respect to the housing (2) for setting a dose of a drug (5) and to be rotated in a dose delivery direction with respect to the housing (2) for delivering the set dose. The dose member (22) comprises a guide feature (46). The guide track (42) is configured to mechanically cooperate with the guide feature (46). The guide track (42) comprises a first section (43A) and a second section (43B) which are connected to each other via a connection region (55). The first section (43A) defines an angular start position (54) for the guide feature (46) and the second section (43B) defines an axial stop position (56) for the guide feature (46). When the dose member (22) is rotated in the dose setting direction, the guide feature (46) is angularly displaced from the angular start position (54) towards the connection region (55), the spring member (26) is torsionally biased, the biased spring member (26) tending to angularly displace the guide feature (46) towards the angular start position (54). When the guide feature (46) has passed the connection region (55), the guide feature (46) enters the second section (43B) and is axially displaced in a proximal direction with respect to the housing (2) towards the axial stop position (56). In the axial stop position, reduction of the torsional bias is prevented by mechanical cooperation of the guide feature (46) and the second section (43B).

15 Claims, 3 Drawing Sheets

ASSEMBLY FOR A DRUG DELIVERY DEVICE

CROSS REFERENCE TO RELATED APPLICATIONS

Figure 1:
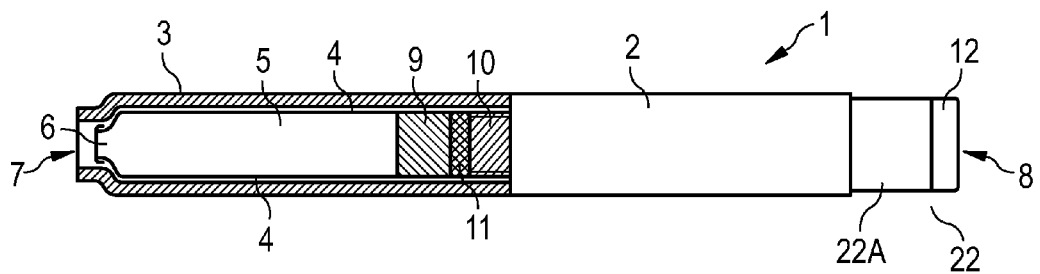

The present application is a 35 U.S.C. 371 National Application of PCT/EP2010/064330 filed Sep. 28, 2010, which claims priority to European Patent Application No. 09171596.1, filed Sep. 29, 2009, the entire contents of which are incorporated entirely herein by reference.

This disclosure relates to an assembly for a drug delivery device.

In a drug delivery device, often, a piston is provided within a cartridge that contains a drug. The piston is displaced with respect to the cartridge by a piston rod for delivering a dose of the drug.

A drug delivery device is, for example, described in document EP 1 923 083 A1.

It is an object of the present disclosure to provide an assembly facilitating provision of a novel, preferably an improved, drug delivery device, for example a device having high dose accuracy and/or with good user-safety.

This object may be achieved by the subject matter of the independent claim. Further features and advantageous embodiments are subject matter of dependent claims.

According to one aspect an assembly for a drug delivery device is provided. The assembly comprises a housing. The assembly comprises a dose member. The dose member may be adapted to be rotated in a dose setting direction with respect to the housing for setting a dose of a drug. The dose member may be adapted to be rotated in a dose delivery direction with respect to the housing for delivering the set dose. The dose delivery direction and the dose setting direction may be opposite rotation directions. The dose member may comprise a guide feature. The assembly may comprise a guide track. The guide track may be configured to mechanically cooperate with the guide feature. The guide track may be axially and rotationally locked with respect to or integrated into the housing. The guide track may comprise a first section. The guide track may comprise a second section. The first section and the second section may be connected to each other via a connection region. The connection region may be part of the guide track. The first section may define an angular start position for the guide feature. In particular, the angular start position of the guide feature may be located within the first section. The guide feature may be in the angular start position before dose setting is commenced. The second section may define an axial stop position for the guide feature. In particular, the axial stop position of the guide feature may be located within the second section. The guide feature may be in the axial stop position after dose setting has been completed. The assembly may comprise a spring member. When the dose member is rotated in the dose setting direction, the guide feature may be angularly displaced from the angular start position towards the connection region. Thereby, the spring member may be torsionally biased. The biased spring member may tend to angularly displace the guide feature towards the angular start position. When the guide feature has passed the connection region, e.g. by an external user-provided force, the guide feature may enter the second section. Within the second section, the guide feature may be axially displaced in a proximal direction with respect to the housing towards the axial stop position. In the axial stop position, reduction of the torsional bias of the spring member may be prevented by mechanical cooperation of the guide feature and the second section. Accordingly, when the guide feature is in the axial stop position, the guide feature may be retained in that position, if no external force is applied.

A further aspect relates to a drug delivery device. The drug delivery device expediently comprises the assembly as described above. The drug delivery device may comprise a cartridge. The cartridge may hold a plurality of doses of a drug. The drug delivery device may be an injection device, preferably an auto-injection device. In an auto-injection device, the injection action is driven by energy which was previously stored within an energy storage member of the device, e.g. the previously mentioned spring member.

The drug delivery device may be a pen-type device. Preferably, the device is a fixed dose device, i.e. a device configured to dispense pre-set doses, in particular doses which may not by varied by the user. Preferably, the drug delivery device enables a manual setting of a dose of the drug. The drug delivery device may be configured to enable an automatic delivery of the set dose of the drug. Hence, an easily handled drug delivery device is provided. The drug may be a liquid medication, such as long-acting or short-acting insulin, heparin and/or growth hormones.

According to an embodiment, the guide track is a slotted guide.

When the guide feature has passed the connection region, the guide feature interacts with the second section, then being displaceable in the proximal direction. The dose member is displaced proximally together with the guide feature. The dose member and the guide feature may be formed unitarily. Alternatively, the guide feature may be rigidly connected with the dose member. Proximal displacement of the dose member with respect to the housing may indicate to the user that the dose has been set correctly.

Preferably, a dose delivery action may be triggered only when the guide feature was brought into mechanical interaction with the second section, i.e. when the dose setting action was performed correctly. Hence, provision of a drug delivery device having high dose accuracy is facilitated.

According to an embodiment, in the axial stop position, the guide feature abuts an axially extending wall of the second section. The torsional bias may keep the guide feature in abutment with the axially extending wall of the second section. Hence, accidental reduction of the torsional bias of the spring member and, thus, rotation of the dose member in the dose delivery direction with respect to the housing is prevented.

In this way, accidental delivery of a dose of the drug may be prevented once the dose setting action has been completed.

According to an embodiment, when mechanically cooperating with the first section, the spring member is pre-biased in the axial direction, preferably the proximal direction, with respect to the housing. Thus, the dose member may be pre-biased in the axial direction by the spring member. The spring member may be pre-biased such that, when the guide feature has passed the connection region, particularly on its way from the first section towards the second section, the spring member may relax in the proximal direction. By relaxing in the proximal direction the spring member may move the guide feature axially in the proximal direction with respect to the housing, for example on account of mechanical cooperation of the spring member with the dose member.

According to an embodiment, the second section extends farther in the proximal direction with respect to the housing than the first section. In particular, the axial stop position may be proximally axially offset with respect to the angular start position. When the guide feature mechanically cooperates with the first section, the guide feature is expediently prevented from being axially displaced towards the axial stop position by the spring member bias due to mechanical cooperation of the guide feature with a proximal side wall of the first section.

According to an embodiment, the first section is oriented transversally with respect to a main longitudinal axis of the housing. The second section may be oriented along the main longitudinal axis of the housing.

The spring member may be or may comprise a coil spring, preferably a helical coil spring. The spring member may be or may comprise a compression spring. The spring member may be a pre-biased, in particular an axially pre-biased, member. When the guide feature interacts with the first section the spring member is prevented from axially relaxing due to mechanical cooperation of the guide feature with the proximal side wall of the first section. Hence, proximal displacement of the guide feature and, hence, of the dose member may be prevented when the guide feature is arranged within the first section of the guide track.

Due to the axial extension of the second section along the main longitudinal axis of the housing, the spring member may relax axially, but preferably not angularly, once the guide feature was moved into interaction with the second section. Thereby, the relaxing spring member displaces the guide feature, and hence, the dose member, automatically proximally. A user-initiated dose delivery action may be possible afterwards.

According to an embodiment, for delivering the set dose, the dose member is axially displaceable in the distal direction with respect to the housing. The guide feature may be distally displaced towards the connection region within the second section. When the guide feature has passed the connection region, torsional bias of the spring member may be reduced. Thereby, the guide feature may be angularly displaced along the first section back towards the angular start position. Accordingly, the dose member may be rotated in the dose delivery direction with respect to the housing. Movement of the dose member in the dose delivery direction may be transformed into distal displacement of the piston with respect to the cartridge in the drug delivery device.

Distal displacement of the dose member with respect to the housing may bring the guide feature back into mechanical interaction with the first section via the connection region.

Once the guide feature has passed the connection region reduction of the torsional bias of the spring member may be enabled and hence, the guide feature is displaced along the first section towards the angular start position. Accordingly, the dose member is rotated in the dose delivery direction for dispensing the set dose.

When distally displacing the dose member, the spring member may be axially biased, e.g. compressed, such that, during a subsequent dose setting action, the spring member may be enabled to displace the guide feature again axially along the second section once the guide feature has passed the connection region and mechanically interacts with the second section. In this way, a drug delivery device which is usable several times for automatically delivering a dose of drug from the same cartridge is achieved.

According to an embodiment, a rotation member is provided. The dose member may be rotationally locked to the rotation member. The dose member may be axially displaceable with respect to the rotation member. The rotation member and the dose member may be splined to one another. Hence, the rotation member may follow rotation of the dose member in the dose setting direction and in the dose delivery direction with respect to the housing. Preferably, the rotation member is secured against axial displacement with respect to the housing.

According to an embodiment, a piston rod is provided. The piston rod may be arranged to drive the piston distally with respect to the cartridge. Rotation of the dose member in the dose delivery direction with respect to the housing may be converted into displacement of the piston rod in the distal direction with respect to the housing.

According to an embodiment, a drive member is provided. The drive member may be adapted to follow rotation of the rotation member in the dose delivery direction with respect to the housing, e.g. by mechanical cooperation with the rotation member. Rotation of the drive member in the dose delivery direction may be converted into displacement of the piston rod in the distal direction with respect to the housing, e.g. by mechanical cooperation of the drive member and the piston rod.

According to an embodiment, a stop member is provided. Rotation of the drive member in the dose setting direction with respect to the housing when the dose member is rotated in the dose setting direction may be prevented by mechanical cooperation of the stop member and the drive member.

Preferably, the drive member and the stop member are coupled, preferably permanently during setting and delivering a dose, to one another by a uni-directional friction clutch mechanism. The clutch mechanism may be configured to prevent relative rotational movement between the drive member and the stop member during rotation of the rotation member in the dose setting direction. The clutch mechanism may be configured to permit relative rotational movement between the stop member and the drive member during rotation of the rotation member in the dose delivery direction.

Accordingly, rotation of the rotation member in the dose delivery direction may be transferred to the drive member such that the drive member rotates in the dose delivery direction. The drive member and the piston rod may be rotationally locked. Preferably, the drive member is splined to the piston rod. The drive member may be threadedly coupled to the housing. In this way, rotation of the drive member in the dose delivery direction may be converted into axial and rotational movement of the piston rod with respect to the housing for dispensing the set dose.

According to an embodiment, the drive member and the rotation member are coupled to one another by a uni-directional friction clutch mechanism. The friction clutch mechanism may comprise a toothing. The toothing may have a plurality of teeth. A respective tooth may comprise a steep side face. The respective tooth may comprise a less steep ramp. The angular extension of the first section may be determined by, preferably correspond to, the distance between the steep side faces of two teeth. The two teeth may be connected to each other via the less steep ramp.

According to an embodiment, the dose member is rotatable only about an angle of less than 360 degrees, preferably less than 180 degrees, in the dose setting direction and in the dose delivery direction with respect to the housing. The angle may be determined by the angular extension of the first section of the guide track.

The distance between the steep side faces of two teeth may define the rotation angle for the rotation of the rotation member with respect to the drive member when setting the dose.

According to a preferred embodiment, an assembly for a drug delivery device is provided. The assembly comprises a housing. The assembly comprises a dose member which is adapted to be rotated in a dose setting direction with respect to the housing for setting a dose of a drug and to be rotated in a dose delivery direction with respect to the housing for delivering the set dose. The dose member comprises a guide feature. The assembly comprises a guide track which is configured to mechanically cooperate with the guide feature. The guide track comprises a first section and a second section which are connected to each other via a connection region. The first section defines an angular start position for the guide feature and the second section defines an axial stop position for the guide feature. The assembly comprises a spring member. When the dose member is rotated in the dose setting direction, the guide feature is angularly displaced from the angular start position towards the connection region and the spring member is torsionally biased. The biased spring member tends to angularly displace the guide feature towards the angular start position. When the guide feature has passed the connection region, the guide feature enters the second section and is axially displaced in a proximal direction with respect to the housing towards the axial stop position. In the axial stop position, reduction of the torsional bias is prevented by mechanical cooperation of the guide feature and the second section.

Due to the assembly described above provision of an easily handled drug delivery device, in particular an auto-injection device, is facilitated which provides high safety for the user.

Of course, features described above in connection with different aspects and embodiments may be combined with each other and with features described below.

Further features and refinements become apparent from the following description of the exemplary embodiments in connection with the accompanying figures.

Figure 2:
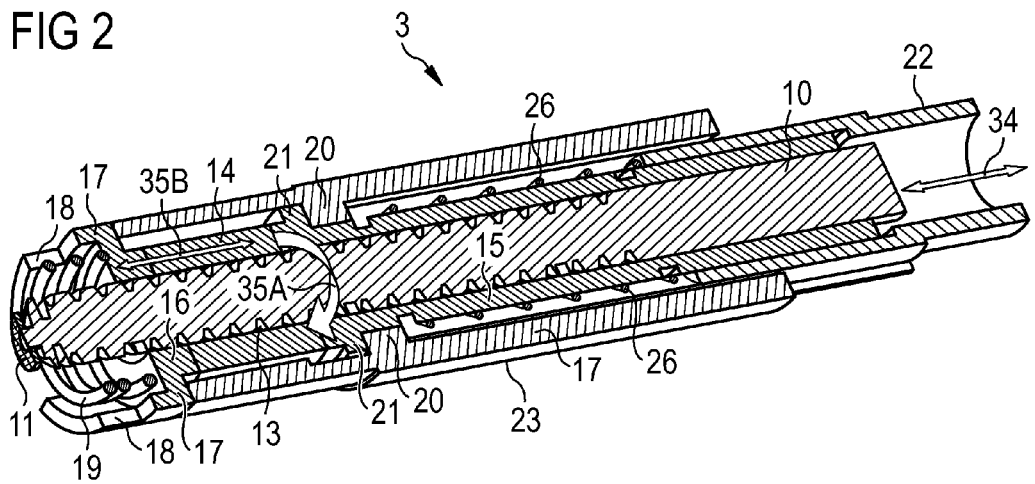
Figure 3:
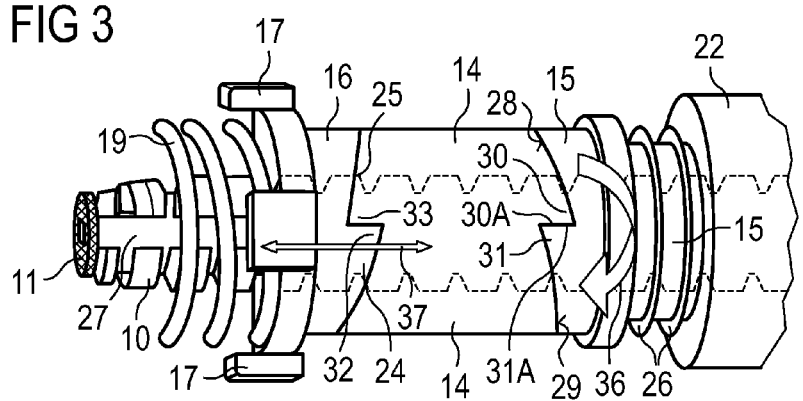
Figure 4:
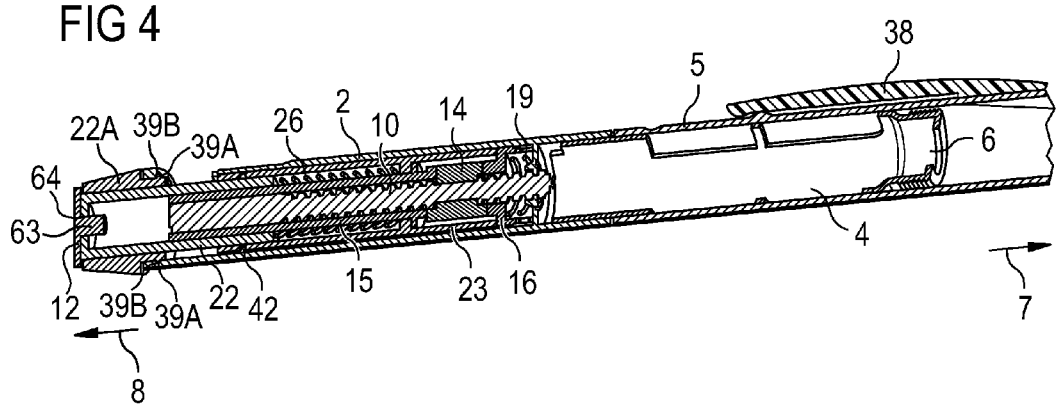
Figure 5:
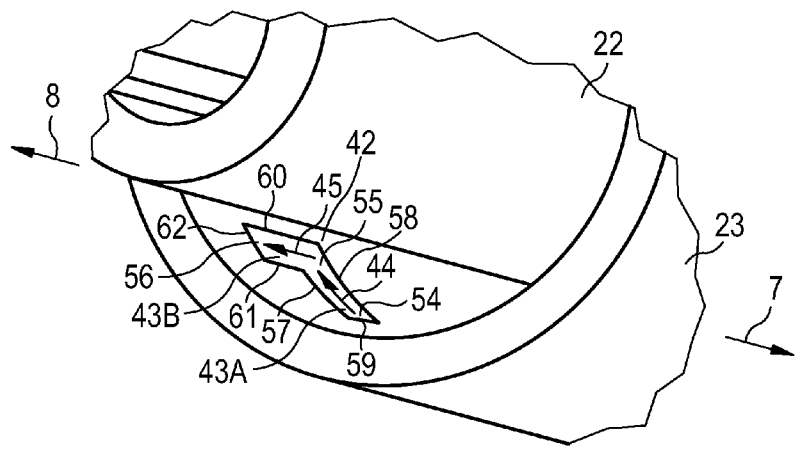
Figure 6:
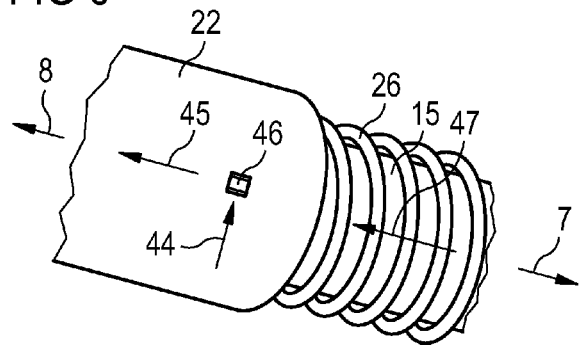
Figure 7:
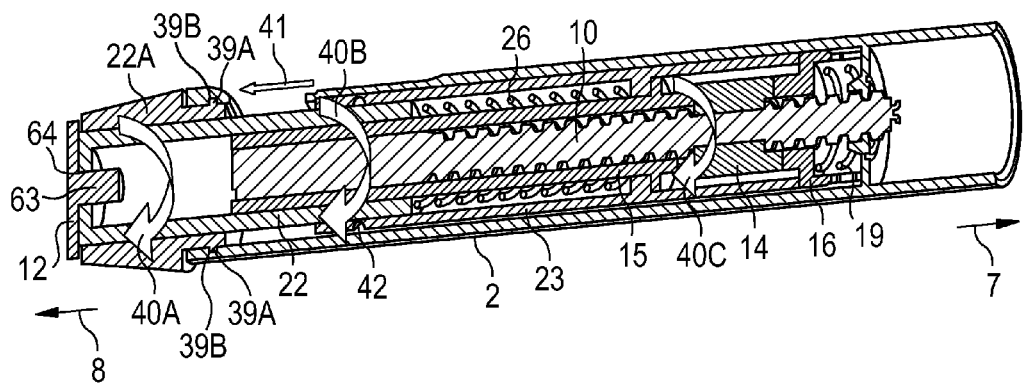
Figure 8:
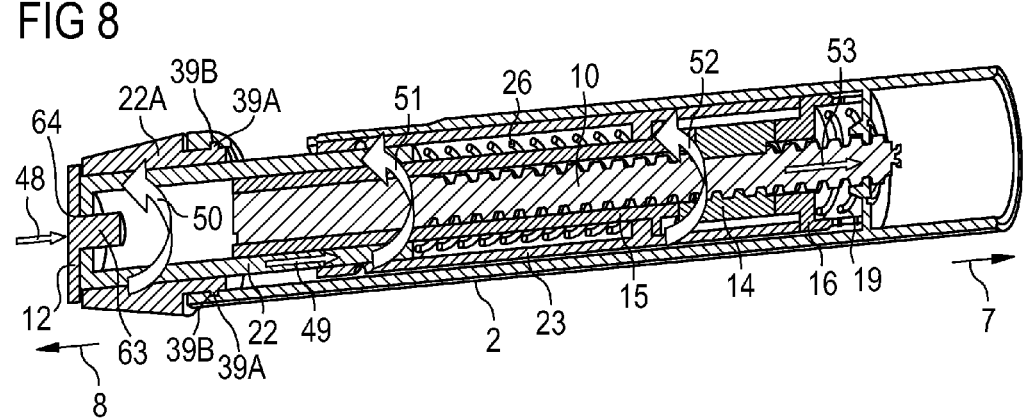

FIG. 1 schematically shows a partly sectional side view of an exemplary embodiment of a drug delivery device, FIG. 2 schematically shows a perspective sectional view of a part of the drug delivery device of FIG. 1, FIG. 3 schematically shows a sectional side view of the part of the drug delivery device shown in FIG. 2, FIG. 4 schematically shows a perspective sectional view of an exemplary embodiment of a drug delivery device, FIG. 5 schematically shows a perspective sectional view of a part of the drug delivery device of FIG. 4, FIG. 6 schematically shows a perspective sectional view of another part of the drug delivery device of FIG. 4, FIG. 7 schematically shows a perspective sectional view of a part of the drug delivery device of FIG. 4 while setting a dose, FIG. 8 schematically shows a perspective sectional view of a part of the drug delivery device of FIG. 4 while dispensing the set dose.

Like elements, elements of the same kind and identically acting elements may be provided with the same reference numerals in the figures.

In FIG. 1, a drug delivery device 1 is shown. The drug delivery device 1 comprises a housing 2. The drug delivery device 1 comprises a cartridge holder 3. The drug delivery device 1 comprises a cartridge 4. The cartridge 4 is retained in the cartridge holder 3. The cartridge holder 3 is attached to the housing 2. Alternatively, the cartridge holder 3 can be dispensed with and the cartridge 4 may be directly secured to the housing 2 of the device 1.

The cartridge 4 may hold a plurality of doses of a drug 5. The drug 5 is preferably a liquid medication, comprising, for example, insulin, like short-acting or long-acting insulin, heparin and/or growth hormones. The cartridge 4 has an outlet 6. The drug 5 can be dispensed from the cartridge 4 through the outlet 6. The outlet 6 may be covered by a membrane. The membrane may protect the drug 5 against external influences during storage of the cartridge 4. The drug delivery device 1 comprises a piston 9. The piston 9 is movably retained in the cartridge 4. The piston 9 is moved with respect to the housing 2 for dispensing a dose of the drug 5.

The drug delivery device 1 comprises a piston rod 10. The piston rod 10 is arranged to drive the piston 9 in a distal direction with respect to the cartridge 4. The drug delivery device 1 comprises a dose member 22. The dose member may comprise a dose setting grip 22A. The dose setting grip 22A may be secured against rotational movement with respect to the dose member 22. The dose member 22 may comprise a dose button 12. The dose button 12 may be configured to be pushed by a user. The dose button 12 may be secured against axial movement with respect to the dose member 22. Preferably, the dose button 12 is secured to the dose member 22 by means of a snap fit connection, which is described in more detail in connection with FIG. 4.

The drug delivery device 1 and the housing 2 have a distal end, which is indicated by arrow 7, and a proximal end, which is indicated by arrow 8. The term "distal end" of the device 1 designates that end of the drug delivery device 1 or a component thereof which is or is to be arranged closest to a dispensing end of the drug delivery device 1. The term "proximal end" of the device 1 designates that end of the device 1 or a component thereof which is or is to be arranged furthest away from the dispensing end of the device 1.

The drug delivery device 1 may be an injection device. The drug delivery device 1 may be a pen-type device, in particular a pen-type injector. The device 1 may be a disposable or a re-usable device. Preferably, the device 1 is configured to dispense fixed doses of the drug 5, i.e. pre-set doses which may not be varied by the user.

Preferably, the device 1 is an auto-injection device, i.e. a device enabling automatic delivery of a set dose of the drug 5 by energy which is stored in an energy storage member of the device 1. The drug delivery device 1 may be a non-electrically, driven device.

The drug delivery device 1 may comprise a needle assembly (not explicitly shown), comprising a needle. The needle assembly may be releasably attached to the distal end of the cartridge holder 3. The membrane may be pierced by the needle for dispensing a dose of the drug 5 from the cartridge 4. Alternatively, the drug delivery device 1 may be a needle-free device.

The housing 2 may be designed to enable a safe and comfortable handling of the drug delivery device 1. The housing 2 may be configured to house, fix, protect and/or guide inner components of the drug delivery device 1, e.g. the piston rod 10 or the dose member 22. Preferably, the housing 2 limits or prevents the exposure of the inner components to contaminants such as liquid, dirt or dust. The housing 2 may be a unitary or a multipart component. The housing 2 may comprise a tubular shape, as shown in FIG. 1. Alternatively, the housing 2 may comprise a non-tubular shape.

The cartridge holder 3 may be, preferably releasably, secured to the housing 2, for example by a threaded connection. The cartridge holder 3 stabilizes the cartridge 4 mechanically. The cartridge holder 3 may be provided with a fixing member (not explicitly shown in FIG. 1), for example snapping means, for securing, preferably releasably securing, the cartridge 4 to the cartridge holder 3.

The piston 9 is retained within the cartridge 4. The piston 9 is movable with respect to the cartridge 4. The piston 9 may seal the cartridge 4 proximally. Movement of the piston 9 in the distal direction with respect to the cartridge 4 causes the drug 5 to be dispensed from the cartridge 4 through the outlet 6.

The piston rod 10 operates through the housing 2 of the drug delivery device 1. The piston rod 10 is designed to transfer axial movement through the drug delivery device 1, for example for the purpose of dispensing the drug 5 (see also FIGS. 2 and 3 for more details). In particular, the piston rod 10 is designed to transfer force to the piston 9, thereby displacing the piston 9 in the distal direction with respect to the cartridge 4 and the housing 2. In this way, a dose of the drug 5 may be dispensed from the cartridge 4 when the outlet 6 was opened, e.g. the membrane was pierced by the needle as described above. The size of the dispensed dose is determined by the distance by which the piston 9 is displaced in the distal direction with respect to the housing 2.

A bearing member 11 may be arranged between the piston 9 and the piston rod 10 to advance the piston 9. The bearing member 11 may be displaced together with the piston rod 10 with respect to the housing 2. The piston rod 10 may be rotatable with respect to the bearing member 11. The bearing member 11 may be axially locked to the piston rod 10.

The piston rod 10 may be made of a flexible or a rigid material. The piston rod 10 may have a circular or a non-circular cross-section. The piston rod 10 may be a simple rod, a lead-screw or the like. The piston rod 10 may be of unitary or multipart construction.

The drug delivery device 1 comprises a drive mechanism. The drive mechanism is described in detail in connection with the description of FIGS. 2 and 3. Dose member 22 may be part of the drive mechanism. The dose member 22 is rotatable with respect to the housing 2. The dose member 22 may be rotated in a dose setting direction with respect to the housing 2 for setting a dose of the drug 5. The dose member 22 may be rotated in a dose delivery direction with respect to the housing 2 when delivering the set dose of the drug 5. The dose setting direction may be clockwise and the dose delivery direction may be counter-clockwise, for example. The dose member 22 may be at least partially axially displaceable with respect to the housing 2 when setting and dispensing a dose, which is described later on in more detail.

A force causing the dose member 22 to be rotated in the dose delivery direction with respect to the housing 2 may be transferred to the piston rod 10 by the drive mechanism. Preferably, the drive mechanism is configured to leave the piston rod 10 stationary with respect to the housing 2 when the dose member 22 is rotated in the dose setting direction with respect to the housing 2. Dose accuracy may be increased in this way.

FIG. 2 schematically shows a perspective sectional view of a part of the drug delivery device of FIG. 1. In particular, FIG. 2 illustrates the drive mechanism of the drug delivery device 1 which was mentioned before.

FIG. 3 schematically shows a sectional side view of the part of the drug delivery device shown in FIG. 2.

The drive mechanism comprises the dose member 22 as mentioned above. The drive mechanism comprises a drive member 14. The drive mechanism comprises a rotation member 15. The drive mechanism comprises a stop member 16.

The drive mechanism is arranged within the housing 2 of the drug delivery device 1. The rotation member 15 may be arranged at least partly inside the dose member 22. The rotation member 15 may be rotationally locked to the dose member 22. Preferably, the rotation member 15 is splined to the dose member 22. Thus, the rotation member 15 follows rotation of the dose member 22 in the dose setting direction with respect to the housing 2 for setting a dose of the drug 5 (see arrow 35A). The rotation member 15 follows rotation of the dose member 22 in the dose delivery direction with respect to the housing 2 for delivering the set dose of the drug 5. The rotation member 15 may be secured against axial displacement with respect to the housing 2 which is described later on in more detail. The dose member 22 is axially displaceable with respect to the rotation member 15 (see arrow 34).

The drive member 14 is rotatable with respect to the housing 2. The dose member 22, the drive member 14 and the rotation member 15 are preferably configured to rotate about a common rotation axis when delivering the dose. The rotation axis may be a main longitudinal axis of the housing 2. Preferably, the rotation axis runs along the piston rod 10 and, in particular, along a main direction of extent of the piston rod 10.

The drive member 14 may be arranged to abut and/or engage the rotation member 15. The rotation member 15 is coupled to the drive member 14 by a uni-directional clutch mechanism, in particular a friction clutch mechanism, for example a slipping clutch. The clutch mechanism is configured to permit rotational movement of the rotation member 15 with respect to the drive member 14 when the rotation member 15 is rotated in the dose setting direction with respect to the housing 2, e.g. when setting a dose of the drug. The clutch mechanism is configured to prevent rotational movement of the rotation member 15 with respect to the drive member 14, when the rotation member 15 is rotated in the dose delivery direction with respect to the housing 2, e.g. when delivering the set dose of the drug 5. Consequently, the drive member 14 follows rotational movement of the rotation member 15 in the dose delivery direction with respect to the housing 2 when delivering the set dose of the drug 5.

The drive member 14 comprises a toothing (see toothing 28 in FIG. 3). Toothing 28 may be arranged at the proximal end section of the drive member 14, for example. The rotation member 15 comprises a toothing (see toothing 29 in FIG. 3). Toothing 29 may be arranged at the distal end section of the rotation member 15, for example. In particular, toothing 29 is arranged at one end section of the rotation member 15 which faces the drive member 14. Toothing 29 and toothing 28 may be configured to mate with each other. Toothing 28 comprises a plurality of teeth (teeth 30 in FIG. 3). Toothing 29 comprises a plurality of teeth (see teeth 31 in FIG. 3). Teeth 30 and teeth 31 may extend along the rotation axis. The rotation axis may be oriented along the main longitudinal axis of the housing 2.

A respective tooth of teeth 30 and teeth 31 may be ramp-shaped, in particular along an azimuthal direction with respect to the rotation axis. The ramp of a respective tooth of teeth 30, 31 may connect a steep side face 30A, 31A with the steep side face of the next tooth of the respective teeth 30, 31. The steep side faces 30A, 31A run parallel to the rotation axis.

When the steep side faces 30A, 31A of two teeth 30, 31 abut and the rotation member 15 is rotated further in the dose delivery direction with respect to the housing 2, the steep side faces 30A, 31A stay in abutment and hence, the drive member 14 follows rotation of the rotation member 15. When the rotation member 15 is rotated in the dose setting direction with respect to the housing 2, toothing 29 of the rotation member 15 slide along the ramps of the teeth 30 of toothing 28, and hence, the rotation member 15 may rotate with respect to the drive member 14. The distance between the steep side faces 30A of two teeth 30 may determine a minimum rotation angle of the rotation member 15 and hence, of the drive member 14.

The drive member 14 may engage the piston rod 10. The drive member 14 is preferably splined to the piston rod 10. The piston rod 10 may comprise a guide notch (not explicitly shown). The drive member 14 may comprise a corresponding guide rib (not explicitly shown) for engaging the guide notch. The splined connection of the drive member 14 and the piston rod 10 may prevent relative rotational movement of the drive member 14 with respect to piston rod 10 and vice versa. Hence, the drive member 14 and the piston rod 10 may be permanently rotationally locked. The piston rod 10 and the drive member 14 may be axially displaced with respect to each other.

The drive member 14 is configured to transfer force, preferably torque, to the piston rod 10. The force transferred may cause the piston rod 10 to be rotated with respect to the housing 2. Additionally or alternatively, the force transferred may cause the piston rod 10 to be displaced in the distal direction with respect to the housing 2 for delivering the set dose of the drug 5. The piston rod 10 comprises a thread 13. The thread 13 may be arranged at an outer surface of the piston rod 10. A mating thread or portion of a thread may be provided inside the housing 2 for a threaded engagement of the housing 2 and piston rod 10. Rotational movement of the piston rod 10 may be converted into axial movement of the piston rod 10 in the distal direction with respect to the housing 2 due to the threaded engagement of the piston rod 10 and the housing 2.

The drive member 14 is arranged between the stop member 16 and the rotation member 15. The stop member 16 is configured to prevent rotational movement of the drive member 14 in the dose setting direction with respect to the housing 2 when the rotation member 15 is rotated in the dose setting direction. Consequently, when setting the dose, the rotation member 15 may rotate with respect to the drive member 14 and with respect to the stop member 16. The stop member 16 is preferably secured against rotation with respect to the housing 2. The stop member 16 may be splined to the housing 2.

The stop member 16 is coupled to the drive member 14 by means of a uni-directional clutch mechanism, for example a slipping clutch. The clutch mechanism prevents rotational movement of the drive member 14 with respect to the stop member 16 when the rotation member 15 rotates in the dose setting direction with respect to the housing, i.e. when setting the dose of the drug 5. The clutch mechanism permits rotational movement of the drive member 14 with respect to the stop member 16 when the rotation member 15 rotates in the dose delivery direction with respect to the housing 2, i.e. when delivering the dose of the drug 5.

The stop member 16 may be arranged to abut or engage the drive member 14, preferably when setting and when delivering the dose. The stop member 16 comprises a toothing (see toothing 32 in FIG. 3). Toothing 32 of the stop member 16 may be arranged at one end section which faces the drive member 14, for example the proximal end section of the stop member 16. Toothing 32 comprises a plurality of teeth 24. The teeth 24 are preferably ramp-shaped. The teeth 24 may be disposed along a perimeter of the stop member 16.

The drive member 14 comprises a further toothing (see toothing 33 in FIG. 3). Toothing 33 is preferably arranged at the distal end section of the drive member 14. Thereby, toothing 28 and toothing 33 of the drive member 14 may be disposed oppositely. Toothing 33 comprises a plurality of teeth 25.

Toothing 33 may be configured in accordance with toothing 29 of the rotation member 15. Toothing 32 and toothing 33 may be configured to cooperate for preventing rotation of the drive member 14 with respect to the housing 2 and with respect to the stop member 16 when setting the dose of the drug 5.

As rotation of the drive member 14 in the dose setting direction with respect to the housing 2 is prevented, movement of the piston rod 10 in the proximal direction with respect to the housing 2, which would require rotation of the drive member 14 in the dose setting direction, is prevented. This may help to increase dose accuracy.

As mentioned previously, the stop member 16 is secured against rotational movement with respect to the housing 2. However, the stop member 16 may be axially displaceable with respect to the housing 2, as indicated by arrow 35B in FIG. 2. For this purpose, the stop member 16 may comprise a plurality of guiding members, for example guide lugs 17. Guide lugs 17 may engage with corresponding guide slots 18. Guide slots 18 may extend axially. The guide slots 18 may be provided in the housing 2.

A guide lug 17 cooperates with a guide slot 18 to prevent rotational movement of the stop member 16 with respect to the housing 2 with axial movement of the stop member 16 with respect to the housing 2 being allowed.

The drive mechanism further comprises a resilient member 19, for example a spring. The resilient member 19 may be biased during dose setting and dose delivery. The resilient member 19 may provide a force keeping the drive member 14 in permanent mechanical cooperation, e.g. engagement, with the stop member 16 and the rotation member 15, when setting and when delivering a dose.

The drive mechanism comprises a support member 20. The support member 20 may be secured against axial and rotational movement with respect to the housing 2. Support member 20 may be unitarily formed with the housing 2. Support member 20 may be a radially inwardly directed protrusion, for example. The rotation member 15 may extend through an opening in support member 20. Support member 20 may provide a counter force to the force exerted by the resilient member 19. On the other side, a counter force may be provided by the distal bearing surface.

The drive mechanism comprises a spring member 26. Spring member 26 may comprise a coil spring like a helical coil spring, for example. Spring member 26 may comprise a pressure spring. Spring member 26 may be arranged at least partly around the rotation member 15. The proximal end of the spring member 26 may cooperate with the dose member 22. The distal end of the spring member 26 may cooperate with the housing 2, in particular bear on the radially inwardly protruding support member 20.

Preferably, the spring member 26 provides torsional flexibility. The spring member may be biased, preferably torsionally biased, during dose setting. Preferably, the spring member 26 provides axial flexibility. Preferably, the spring member 26 is pre-biased in the proximal direction with respect to the housing 2 before setting a dose of the drug 5. Functionality of the spring member 26 will be described later on in connection with the description of FIGS. 6 to 8.

The rotation member 15 comprises a protruding portion 21. The protruding portion 21, e.g. a flange portion, may protrude radially outwardly from the rotation member 15. The protruding portion 21 may be configured to abut support member 20.

The drive member 14, the rotation member 15, the stop member 16, and the dose member 22 may comprise or may be embodied as a sleeve, respectively. The piston rod 10 may be arranged and/or driven through at least one or more, or all of said sleeves.

FIG. 4 schematically shows a perspective sectional view of an exemplary embodiment of a drug delivery device.

According to this embodiment, an inner sleeve 23 is arranged within the housing 2. Inner sleeve 23 may be secured against translational and rotational movement with respect to the housing 2. The drive mechanism (see FIGS. 2 and 3) may be arranged within the inner sleeve 23.

The dose member 22 may be, in particular in a limited fashion, rotationally and axially displaceable with respect to the inner sleeve 23 for setting and delivering a dose, which is described later on in more detail. The dose member 22 may be secured to the inner sleeve 23 by means of a guide track 42 and a guide feature 46 (see also FIGS. 5 and 6). The guide track 42 is preferably arranged at an inner surface of the inner sleeve 23. Alternatively, the guide track 42 is arranged at an inner surface of the housing 2. In this case, the inner sleeve 23 may be redundant. Functionality of the guide track 42 and the guide feature 46 will be described in connection with the description of FIGS. 5 to 8.

The dose setting grip 22A may be arranged at a proximal end section of the dose member 22. The dose setting grip 22A may be configured to be gripped by the user for rotating the dose member 22 in the dose setting direction with respect to the housing 2 for setting a dose of the drug 5. The dose setting grip 22A may be a sleeve within which the dose member 22 is arranged.

The dose setting grip 22A is secured against rotational movement with respect to the dose member 22. The dose member 22 is axially displaceable with respect to the dose setting grip 22A. Preferably, the dose setting grip 22A is splined to the dose member 22.

The dose setting grip 22A may be secured to the housing 2 for example by means of a snap-fit connection. The dose setting grip 22A may comprise engaging means 39A. Engaging means 39A may comprise a protrusion arranged at an outer surface of the dose setting grip 22A, for example. The housing 2 may comprise mating engaging means 39B, for example a guide slot. Mating engaging means 39B may be arranged at an inner surface of the housing 2. Due to mechanical cooperation of engaging means 39A and mating engaging means 39B, the dose setting grip 22A is axially secured to the housing 2. The dose setting grip 22A is rotatable with respect to the housing 2, preferably only in a limited fashion. The rotation angle of the dose setting grip 22A with respect to the housing 2 may be determined by the angular extension of the mating engaging means 39B, e.g. the guide slot. Alternatively or additionally, the rotation angle may be determined by the axial extension of a first section 43A of the guide track 42, which is described in connection with FIGS. 5 and 6.

The dose button 12 may be arranged at the proximal end section of the dose member 22. The dose button 12 may be axially locked to the dose member 22 and the dose member 22 may be rotatable with respect to the dose button 12. The dose button 12 comprises engaging means 63. Engaging means 63 may comprise a protrusion, for example. The dose member 22 may comprise mating engaging means 64. Engaging means 64 may comprise an indentation, for example. Due to mechanical cooperation of engaging means 63 and mating engaging means 64 the dose button 12 is axially secured to the dose member 22. However, the dose member 22 is rotatable with respect to the dose button 12, in particular when delivering the dose.

FIG. 5 schematically shows a perspective sectional view of a part of the drug delivery device of FIG. 4. In particular, FIG. 5 shows the inner surface of the inner sleeve 23. Additionally, FIG. 5 shows an outer surface of the dose member 22.

FIG. 6 schematically shows a perspective sectional view of a part of the drug delivery device of FIG. 4. In particular, FIG. 6 shows the outer surface of the dose member 22.

The dose member 22 comprises a guide feature 46 (see FIG. 6). The guide feature 46 may be arranged at an outer surface of the dose member 22. Preferably, the guide feature 46 is arranged in the distal end section of the dose member 22.

The guide feature 46 protrudes radially outwardly from the dose member 22. The guide feature 46 may be a lug, for example. The guide feature 46 may be pin-like. Preferably, the guide feature 46 is unitarily formed with the dose member 22. Alternatively, the guide feature 46 may be rigidly connected to the dose member 22. The guide feature 46 is secured against translational and rotational movement with respect to the dose member 22.

The inner sleeve 23 comprises the guide track 42 as mentioned above. The guide track 42 is secured against translational and rotational displacement with respect to the housing 2. Preferably, the guide track 42 is part of the inner sleeve 23. The guide track 42 may be a slotted guide, for example. The guide track 42 may be shaped L-like or may comprise an L-like shaped portion. Preferably, the guide track 42 is milled or moulded into the inner sleeve 23.

The guide track 42 is configured to mechanically cooperate with the guide feature 46. In particular, the guide feature 46 is guided along the guide track 42 for setting and delivering a dose of the drug 5 which is described later on in more detail. The guide track 42 may retain the guide feature 46 and delimit the range of movement of the dose member 22 with respect to the housing 2, in particular angularly as well as axially.

The guide track 42 comprises a first section 43A. The first section 43A runs transversally, preferably perpendicularly, with respect to the main longitudinal axis of the housing 2. Preferably, the first section 43A runs along the angular direction as seen from the main longitudinal axis of the housing 2. The angular extension of the first section 43A may be less than or equal to the angular extension of the engaging means 39B, e.g. the guide slot.

The first section 43A comprises a proximal side wall 57. The first section comprises a distal side wall 58. The proximal side wall 57 and the distal side wall 58 are connected by an axially extending end wall 59.

The guide track 42 comprises a second section 43B. Preferably, the second section 43B runs along the main longitudinal axis of the housing 2. Preferably, the second section 43B runs perpendicularly with respect to the first section 43A. The second section 43B comprises a first axially extending side wall 60 and a second axially extending side wall 61. The side walls 60 and 61 are connected by a proximal end wall 62.

A connection region 55 is arranged between the first section 43A and the second section 43B. The first section 43A and the second section 43B are connected to each other via the connection region 55. When the guide feature 46 mechanically interacts with the connection region 55 a transition of the guide feature 46 from the first section 43A into the second section 43B and vice versa is possible. A transition from the first section 43A into the second section 43B and vice versa may be blocked aside from via the connection region 55 due to mechanical cooperation of the guide feature 46 with the proximal side wall 57 of the first section 43A or the axially extending side wall 61 of the second section 43B.

The first section 43A may define an angular start position 54 for the guide feature 46. In particular, the angular start position 54 of the guide feature 46 may be located within the first section 43A. In the angular start position 54, the guide feature 46 may abut the axially extending end wall 59. Before setting a dose of the drug 5, the guide feature 46 may be positioned in the angular start position.

The second section 43B may define an axial stop position 56 for the guide feature 46. In particular, the axial stop position 56 of the guide feature 46 may be located within the second section 43B. In the axial stop position 56, the guide feature 46 may abut the proximal end wall 62. After setting of the dose was completed, the guide feature 46 may be positioned in the axial stop position 56.

Preferably, the second section 43B extends farther in the proximal direction with respect to the housing 2 than the first section 43A. Hence, the axial stop position 56 may be proximally axially, and preferably angularly, offset with respect to the angular start position 54. Consequently, when the guide feature 46 is guided from the first section 43A into the second section 43B, the guide feature 46 and, hence, the dose member 22, may be proximally displaced with respect to the housing 2.

The first section 43A comprises the proximal side wall 57 as described above. The axially biased spring member 26, which was described in connection with FIG. 3, may push the guide feature 46 against the proximal side wall 57, when the guide feature 46 cooperates with the first section 43A. The proximal side wall 57 may limit displacement of the guide feature 46 and, hence, of the dose member 22, in the proximal direction with respect to the housing 2. Consequently, when the guide feature 46 mechanically cooperates with the first section 43A, the guide feature 46 is prevented from being axially displaced towards the axial stop position 56 by mechanical cooperation of the guide feature 46 with the proximal side wall 57. When the guide feature 46 interacts with the first section 43A, the guide feature 46 may be only angularly displaceable with respect to the housing 2.

The second section 43B comprises the axially extending side walls 60 and 61 as described above. The guide feature 46 may abut one side wall, in particular the side wall 61 being arranged angularly closer to the first section 43A, when mechanically cooperating with the second section 43B. The axially extending side wall 61 may limit angular displacement of the guide feature 46 towards the angular start position 54. When the guide feature 46 interacts with the second section 43B, the guide feature 46 may be only axially displaceable with respect to the housing 2.

For setting a dose of the drug 5, the guide feature 46 may be guided from the angular start position 54 via the connection region 55 and towards the axial stop position 56. For delivering the set dose of the drug 5 the guide feature 46 may be guided from the axial stop position 56 via the connection region 55 and back towards the angular start position 54. Hence, for setting and delivering the dose the guide feature 46 is guided along the same path but in the opposite direction along the guide track 42. Operation of setting and delivering a dose will be described in connection with FIGS. 7 and 8.

FIG. 7 schematically shows a perspective sectional view of a part of the drug delivery device of FIG. 4 while setting a dose.

For setting a dose of the drug 5 the user may grip the dose setting grip 22A. The user may rotate the dose setting grip 22A (see arrow 40A) and, hence, the dose member 22 (see arrow 40B), which is rotationally locked with the dose setting grip 22A, in the dose setting direction with respect to the housing 2. Thereby, the guide feature 46 is angularly displaced away from the angular start position 54 along the first section 43A towards the connection region 55, as indicated by arrow 44 in FIGS. 5 and 6.

Due to rotation of the dose member 22 the spring member 26 is torsionally biased. The torsionally biased spring member 26 may tend to angularly displace the guide feature 46 back towards the angular start position 54. Accordingly, when the user releases the dose setting grip 22A before the dose has been set completely, in particular before the guide feature 46 has passed the connection region 55 and mechanically interacts with the second section 43B, the dose member 22 is rotated in the opposite direction and, hence, the guide feature 46 is automatically displaced back into the angular start position 54 due to the spring member 26 torsionally relaxing. In this way, dispensing of a not correctly, in particular not completely, set dose of the drug 5 may be prevented.

The dose setting grip 22A and, hence, the dose member 22, is further rotatable in the dose setting direction until the guide feature 46 has passed into the connection region 55. The dose setting grip 22A and, hence, the dose member 22 may be rotatable only about an angle of less than 360 degrees, preferably by an angle of less than 180 degrees, in the dose setting direction with respect to the housing 2. The dose setting grip 22A, in particular the dose member 22, is rotated by 45 degrees with respect to the housing 2 for setting the dose, for example. The angle by which the dose member 22 is rotated may be determined by the angular extension of the first section 43A. The angular extension of the first section 43A may be determined by, preferably may correspond to, the distance between the steep side faces 31A of two teeth 31 of the rotation member 15. Hence, for setting a dose of the drug 5 the rotation member 15 and the dose member 22 may be rotated about the same angle (see arrow 40C).

The rotation member 15 rotates with respect to the drive member 14 and with respect to the stop member 16. As the piston rod 10 is coupled, preferably splined, to the drive member 14, the piston rod 10 is prevented from being moved with respect to the housing 2 by mechanical interaction of the stop member 16 and the drive member 14. Dose accuracy can be increased in this way.

When the guide feature 46 interacts with the first section 43A, proximal displacement of the dose member 22 is prevented due to mechanical cooperation of the guide feature 46 and the proximal wall 57 of the first section 43A as described in connection with FIG. 5. When the guide feature 46 interacts with the first section 43A, the drug delivery device 1 is in a non-delivery mode.

Once having passed the connection region 55 the guide feature 46 may cooperate with the second section 43B. Then the axially biased spring member 26 may relax (see arrow 47, FIG. 6) in the proximal direction. Thereby, the dose member 22, and, hence, the guide feature 46 (see arrow 45 in FIGS. 5 and 6), is automatically displaced in the proximal direction with respect to the housing 2 and with respect to the dose setting grip 22A (arrow 41). In particular, the guide feature 46 is moved along the second section 43B towards the axial stop position 56.

When the guide feature 46 is in the axial stop position 56 it abuts the proximal end wall 62. Hence, further displacement of the dose member 22 in the proximal direction with respect to the housing 2 is prevented when the guide feature 46 is in the axial stop position 56. Due to the proximal displacement of the dose member 22 with respect to the dose setting grip 22A, the dose button 12 is displaced proximally with respect to the dose setting grip 22A. This proximal displacement may bring the dose button 12 into a position, in which the user may press the dose button 12 distally for dispensing the set dose. The dose setting action may now be completed and the device 1 may be in a dose delivery mode. In particular, distal displacement of the dose button 12 and, hence, of the dose member 22, for delivering the set dose may be enabled only when the guide feature 46 is in the axial stop position 56.

In the second section 43B the guide feature 46 cooperates with the axially extending side wall 61. In particular, torsional bias of the spring member 26, which was built up during rotation of the dose member 22 in the dose setting direction, may keep the guide feature 46 in abutment with the axially extending side wall 61 of the second section 43B.

Reduction of the torsional bias of the spring member 26 may be prevented due to mechanical cooperation of the guide feature 46 and the axially extending side wall 61. Hence, angular displacement of the guide feature 46 towards the angular start position 54 and, thus, rotation of the dose member 22 in a direction opposite to the dose setting direction, e.g. in the dose delivery direction, may be prevented due to interaction of the guide feature 46 with the axially extending side wall 61 of the second section 43B. In this way, unintentional delivery of the dose may be prevented. Once the guide feature 46 interacts with the second section 43B, the user may release the dose setting grip 22A.

Due to mechanical cooperation of the guide feature 46 and the axially extending side wall 60 of the second section 43B, angular displacement of the guide feature 46 and, thus, further rotation of the dose setting grip 22A and, hence, of the dose member 22 in the dose setting direction with respect to the housing 2 may be prevented once the guide feature 46 mechanically interacts with the second section 43B.

FIG. 8 schematically shows a perspective sectional view of a part of the drug delivery device of FIG. 4 while dispensing the set dose.

For dispensing the set dose of the drug 5 the user may push onto the dose button 12 of the dose member 22 (see arrow 48) for displacing it in the distal direction with respect to the housing 2 and, in particular, with respect to the dose setting grip 22A. As described previously, the dose button 12 is secured against axial movement with respect to the dose member 22. However, the dose member 22 may rotate with respect to the dose button 12.

When pushing the dose button 12 distally, the dose member 22 is displaced in the distal direction with respect to the housing 2 and with respect to the dose setting grip 22A. In particular, the dose member 22 is displaced distally by the same distance for delivering the dose as the dose member 22 was displaced proximally when setting the dose of the drug 5. When the dose member 22 is displaced distally, the spring member 26 may be (re-)biased in the axial direction.

During distal displacement of the dose member 22, the guide feature 46 is guided along the second section 43B away from the axial end position and towards the connection region 55, reduction of the torsional bias of the spring member 26 thereby being prevented due to mechanical cooperation of the guide feature 46 and the axially extending side wall 61 of the second section 43B as described previously.

When the guide feature 46 has passed the connection region 55, the guide feature 46 may mechanically interact with the first section 43A, e.g. abut the distal side wall 58. The torsionally biased spring member 26, which was prevented from relaxing when the guide feature 46 was mechanically cooperating with the second section 43B due to the axially extending side wall 61, may relax once the guide feature 46 has entered the first section 43A. Thus, the spring member 26 automatically angularly displaces the guide feature 46 along the first section 43A towards the angular start position 54.

The dose member 22 is automatically rotated in the dose delivery direction with respect to the housing 2 by the energy which was previously stored in the spring member 26 (see arrow 50). The dose member 22 is rotated by the same angle in the dose delivery direction as the dose member 22 was rotated in the dose setting direction for setting the dose of the drug 5. As described previously, the rotation angle of the dose member 22 is determined by the angular extension of the first section 43A. When the guide feature 46 has reached the angular start position 54, the guide feature 46 abuts the axially extending end wall 59. Consequently, the dose member 22 is prevented from rotating further in the dose delivery direction when the guide feature 46 is in the angular start position 54.

When the dose member 22 rotates in the dose delivery direction the rotation member 15 rotates in the dose delivery direction, as indicated by arrow 51. The drive member 14 follows rotation of the rotation member 15 in the dose delivery direction with respect to the housing 2 and with respect to the stop member 16 (see arrow 52). The rotation angle of the rotation member 15 and, hence, of the drive member 14 is determined by the distance between the steep side faces 30A, 31A of the respective teeth 30, 31.

Rotation of the drive member 14 in the dose delivery direction is converted into rotation of the piston rod 10 in the dose delivery direction. The rotation of the piston rod 10 is converted into movement of the piston rod 10 in the distal direction with respect to the housing 2 (see arrow 53), e.g. by the threaded connection of the piston rod 10 and the housing 2. Accordingly, the piston 9 is displaced in the distal direction with respect to the cartridge 4.

The drug delivery device 1 described above may provide a high dose accuracy. The drug delivery device 1 may for example be configured for setting and delivering doses of 30 IU or greater, for example a dose of 50 IU or greater, thereby providing high dose accuracy. Alternatively, the drug delivery device 1 may provide doses of 5 IU or less or any dose in-between while having good dose accuracy. If the device 1 was to be designed for doses less than 1 IU, the number of teeth 30, 31 of the respective toothing 28, 29 of drive member 14 and rotation member 15 should be increased.

Other implementations are within the scope of the following claims. Elements of different implementations may be combined to form implementations not specifically described herein.

REFERENCE NUMERALS

1 Drug delivery device
2 Housing
3 Cartridge holder
4 Cartridge
5 Drug
6 Outlet
7 Distal end
8 Proximal end
9 Piston
10 Piston rod
11 Bearing member
12 Dose button
13 Thread
14 Drive member
15 Rotation member
16 Stop member
17 Guide feature
18 Guide slot
19 Resilient member
20 Support member
21 Protruding portion
22 Dose member
22A Dose setting grip
23 Inner sleeve
24 Tooth
25 Tooth
26 spring member
27 Guide notch
28 Toothing
29 Toothing
30 Tooth
30A Steep side face
31 Tooth
31A Steep side face
32 Toothing
33 Toothing
34 Arrow
35A Arrow
35B Arrow 36 Arrow
37 Arrow
38 Cap
39A Engaging means
39B Engaging means
40 Arrow
41 Arrow
42 Guide track
43A First section
43B Second section
44 Arrow
45 Arrow
46 Guide feature
47 Arrow
48 Arrow
49 Arrow
50 Arrow
51 Arrow
52 Arrow
53 Arrow
54 Angular start position
55 Connection region
56 Axial stop position
57 Proximal side wall
58 Distal side wall
59 Axial end wall
60 Axial side wall
61 Axial side wall
62 Proximal end wall
63 Engaging means
64 Engaging means

The invention claimed is:

1. An assembly for a drug delivery device, comprising:
a housing,
a dose member adapted to be rotated in a dose setting direction with respect to the housing for setting a dose of a drug and to be rotated in a dose delivery direction with respect to the housing for delivering the set dose, the dose member comprising a guide feature,
a guide track configured to mechanically cooperate with the guide feature, the guide track comprising a first section and a second section which are connected to each other via a connection region, wherein the first section defines an angular start position for the guide feature and the second section defines an axial stop position for the guide feature, and
a spring member,
wherein, when the dose member is rotated in the dose setting direction, the guide feature is angularly displaced from the angular start position towards the connection region, the spring member is torsionally biased, the biased spring member tending to angularly displace the guide feature towards the angular start position, and wherein, when the guide feature has passed the connection region, the guide feature enters the second section and is axially displaced in a proximal direction with respect to the housing towards the axial stop position, and, in the axial stop position, reduction of the torsional bias is prevented by mechanical cooperation of the guide feature and the second section.

2. The assembly of claim 1, wherein, when mechanically cooperating with the first section, the spring member is pre-biased in the axial direction with respect to the housing such that, when the guide feature has passed the connection region, the spring member relaxes in the proximal direction, thereby moving the guide feature axially in the proximal direction with respect to the housing.

3. The assembly of claim 1, wherein, in the axial stop position, the guide feature abuts an axially extending wall of the second section such that reduction of the torsional bias of the spring member and, thus, rotation of the dose member in the dose delivery direction with respect to the housing is prevented.

4. The assembly according to claim 1, wherein the guide track is secured against translational and rotational displacement with respect to the housing, and wherein the first section runs transversally with respect to a main longitudinal axis of the housing and the second section runs along the main longitudinal axis.

5. The assembly according to claim 1, wherein the second section extends farther in the proximal direction with respect to the housing than the first section such that the axial stop position is proximally axially offset with respect to the angular start position, and wherein, when the guide feature mechanically cooperates with the first section, the guide feature is prevented from being axially displaced towards the axial stop position by mechanical cooperation of the guide feature with a proximal side wall of the first section.

6. The assembly according to claim 1, wherein, for delivering the set dose, the dose member is axially displaceable in the distal direction with respect to the housing the guide feature being distally displaceable towards the connection region, within the second section wherein, when the guide feature has passed the connection region, torsional bias of the spring member is reduced, thereby angularly displacing the guide feature along the first section back towards the angular start position and rotating the dose member in the dose delivery direction with respect to the housing.

7. The assembly according to claim 1, wherein distal displacement of the dose member is prevented when the guide feature is arranged within the first section of the guide track.

8. The assembly according to claim 1, comprising a rotation member, wherein the dose member is rotationally locked to the rotation member, and wherein the dose member is axially displaceable with respect to the rotation member.

9. The assembly according to claim 1, comprising a piston rod, wherein rotation of the dose member in the dose delivery direction with respect to the housing is converted into displacement of the piston rod in the distal direction with respect to the housing.

10. The assembly of claim 8, comprising
a drive member which is adapted to follow rotation of the rotation member in the dose delivery direction with respect to the housing, rotation of the drive member in the dose delivery direction being converted into displacement of the piston rod in the distal direction with respect to the housing by mechanical cooperation of the drive member and the piston rod,
a stop member, wherein rotation of the drive member in the dose setting direction with respect to the housing when the dose member is rotated in the dose setting direction is prevented by mechanical cooperation of the stop member and the drive member.

11. The assembly of claim 10, wherein the drive member and the rotation member are coupled to one another by a first uni-directional friction clutch mechanism, the first friction clutch mechanism comprising a toothing having a plurality of teeth, a respective tooth comprising a steep side face, wherein the angular extension of the first section corresponds to the distance between the steep side faces of two teeth.

12. The assembly of claim 11, wherein the drive member and the stop member are coupled to one another by a second uni-directional friction clutch mechanism, which is configured to prevent relative rotational movement between drive member and stop member during rotation of the rotation member in the dose setting direction and to permit relative rotational movement between the stop member and the drive member during rotation of the rotation member in the dose delivery direction.

13. The assembly according to claim 1, wherein the dose member is rotatable only about an angle of less than 360 degrees in the dose setting direction and in the dose delivery direction with respect to the housing, the angle being determined by the angular extension of the first section of the guide track.

14. The assembly according to claim 1, wherein the guide track is a slotted guide.

15. A drug delivery device comprising the assembly according to claim 1 and a cartridge, the cartridge holding a plurality of doses of the drug, wherein the drug delivery device is an auto-injection device.

* * * * *